United States Patent
Kujawski

(10) Patent No.: US 7,465,316 B2
(45) Date of Patent: Dec. 16, 2008

(54) TRI-PETALED AORTIC ROOT VASCULAR GRAFT

(75) Inventor: Dennis Kujawski, Warwick, NY (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 481 days.

(21) Appl. No.: 10/823,061

(22) Filed: Apr. 12, 2004

(65) Prior Publication Data

US 2005/0228487 A1   Oct. 13, 2005

(51) Int. Cl.
*A61F 2/06* (2006.01)
(52) U.S. Cl. .................... 623/1.31; 623/1.51
(58) Field of Classification Search ............... 623/1.26
See application file for complete search history.

(56) References Cited

U.S. PATENT DOCUMENTS

| | | |
|---|---|---|
| 2,978,787 A | 4/1961 | Liebig |
| 3,096,560 A | 7/1963 | Liebig |
| 4,047,252 A | 9/1977 | Liebig et al. |
| 4,193,137 A | 3/1980 | Heck |
| 4,517,687 A | 5/1985 | Liebig et al. |
| 4,530,113 A | 7/1985 | Matterson |
| 4,695,280 A | 9/1987 | Watanabe et al. |
| 4,743,250 A | 5/1988 | Kitagawa et al. |
| 4,892,539 A | 1/1990 | Koch |
| 4,969,896 A | 11/1990 | Shors |
| 5,139,515 A | 8/1992 | Robicsek |
| 5,156,619 A * | 10/1992 | Ehrenfeld ............ 623/1.31 |
| 5,178,630 A | 1/1993 | Schmitt |
| 5,178,634 A | 1/1993 | Ramos Martinez |
| 5,282,846 A | 2/1994 | Schmitt |
| 5,282,847 A | 2/1994 | Trescony et al. |
| 5,314,468 A | 5/1994 | Ramos Martinez |
| 5,370,682 A | 12/1994 | Schmitt |
| 5,383,925 A | 1/1995 | Schmitt |
| 5,413,598 A | 5/1995 | Moreland |
| 5,476,506 A | 12/1995 | Lunn |
| 5,509,931 A | 4/1996 | Schmitt |
| 5,628,786 A | 5/1997 | Banas et al. |
| 5,653,746 A | 8/1997 | Schmitt |

(Continued)

FOREIGN PATENT DOCUMENTS

EP   1 230 901   8/2002

(Continued)

*Primary Examiner*—William H Matthews
(74) *Attorney, Agent, or Firm*—Hoffman & Baron, LLP

(57) ABSTRACT

An implantable, flat-woven multi-petaled graft includes (i) a hollow tubular woven portion having opposed first and second tubular ends, the woven portion having a number of warp yarns interlaced with a number of fill yarns in a flat-woven tubular woven pattern to define a flat-woven tubular diameter, and (ii) a bulbous woven portion having opposed first and second ends, the first bulbous end having a greater number of warp yarns interlaced with the fill yarns in a flat-woven tubular bulbous pattern contiguously woven from the second tubular end to provide a seamless woven, wherein the greater number of warp yarns are threadingly engaged with the fill yarns to define a flat-woven bulbous diameter; wherein the second end of the bulbous portion is scalloped with a plurality of petal-like projections seamlessly woven from the first bulbous end. The graft may include three petal-like projections. The bulbous woven section may be truncated, i.e., hemispherically or hemibulbously shaped.

22 Claims, 1 Drawing Sheet

U.S. PATENT DOCUMENTS

| | | |
|---|---|---|
| 5,697,969 A | 12/1997 | Schmitt et al. |
| 5,697,970 A | 12/1997 | Schmitt et al. |
| 5,741,332 A | 4/1998 | Schmitt |
| 5,769,884 A | 6/1998 | Solovay |
| 5,800,514 A | 9/1998 | Nunez et al. |
| 5,824,047 A | 10/1998 | Moreland |
| 5,843,158 A | 12/1998 | Lenker et al. |
| 5,861,026 A | 1/1999 | Harris et al. |
| 5,891,195 A | 4/1999 | Klostermeyer et al. |
| 5,904,714 A | 5/1999 | Nunez et al. |
| 5,913,894 A | 6/1999 | Schmitt |
| 6,090,137 A | 7/2000 | Schmitt |
| 6,136,022 A | 10/2000 | Nunez et al. |
| 6,176,875 B1 | 1/2001 | Lenker et al. |
| 6,193,754 B1 | 2/2001 | Seedhom |
| 6,342,070 B1 | 1/2002 | Nguyen-Thien-Nhon |
| 6,347,632 B1 | 2/2002 | Eberhardt et al. |
| 6,352,554 B2 | 3/2002 | DePaulis |
| 6,461,382 B1 | 10/2002 | Cao |
| 6,544,285 B1 | 4/2003 | Thubrikar et al. |
| 6,547,820 B1 | 4/2003 | Staudenmeier |
| 6,554,855 B1 | 4/2003 | Dong |
| 6,596,023 B1 | 7/2003 | Nunez et al. |
| 6,648,900 B2 | 11/2003 | Fleischman et al. |
| 6,648,901 B2 | 11/2003 | Fleischman et al. |
| 6,702,828 B2 | 3/2004 | Whayne |
| 2001/0049553 A1 | 12/2001 | De Paulis |
| 2003/0078650 A1* | 4/2003 | Nunez et al. ............... 623/1.51 |
| 2003/0139805 A1* | 7/2003 | Holmberg et al. .......... 623/1.31 |
| 2004/0019375 A1 | 1/2004 | Casey, II et al. |
| 2004/0049264 A1 | 3/2004 | Sowinski et al. |

FOREIGN PATENT DOCUMENTS

| | | |
|---|---|---|
| WO | WO 01/52776 | 7/2001 |

* cited by examiner

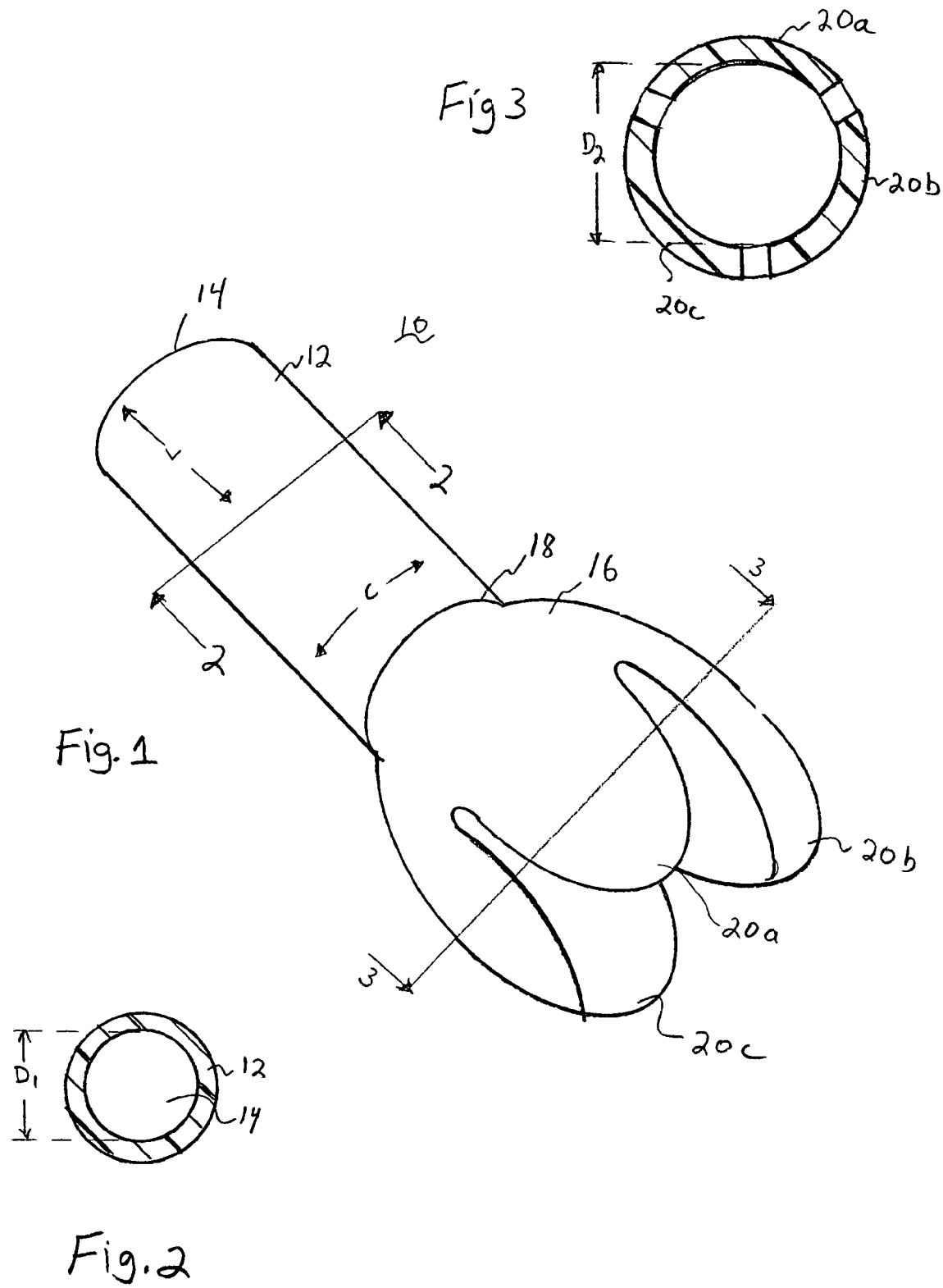

TRI-PETALED AORTIC ROOT VASCULAR GRAFT

FIELD OF THE INVENTION

The present invention relates to an aortic root vascular graft and methods of manufacture. In particular, the present invention relates to seamlessly woven, tri-petaled, aortic root vascular grafts.

BACKGROUND OF THE INVENTION

Tubular woven fabrics have been used for soft-tissue implantable prostheses to replace or repair damaged or diseased lumens in the body. In particular, endoprostheses are used in the vascular system to prevent the blood from rupturing a weakened section of the vessel. Such endoluminal conduits are generally affixed in a specified location in the vessel by means of stents, hooks or other mechanisms which serve to secure the device in place. Endoluminal tubular devices or conduits can also be used in other lumens in the body, such as in the esophagus and colon areas.

Weaving is commonly employed to fabricate various tubular shaped products. For example, implantable tubular prostheses which serve as conduits, such as vascular grafts, esophageal grafts and the like, are commonly manufactured using tubular weaving techniques, wherein the tubular product is woven as a flat tube. In such weaving processes, a variety of yarns are interwoven to create the tubular fabric. For example, a set of warp yarns is used which represents the width of the product being woven, and a fill yarn is woven between the warp yarns. The fill yarn is woven along the length of the warp yarns, with each successive pass of the fill yarn across the warp yarns for each side of the tube representing one machine pick. Thus, two machine picks represent one filling pick in a tubular woven structure, since weaving one fill yarn along the entire circumference of the tube, i.e., one filling pick, requires two picks of the weaving machine. As such, in a conventional woven product, the fill yarn is woven along the length of the warp yarns for a multiple number of machine picks, with the woven product produced defined in length by the number of filling picks of the fill yarn and defined in width by the number of warp yarns in which the fill yarn is woven therebetween.

Some damaged or diseased lumens, however, have quite complex shapes. For example, the root portion of the aorta is provided sinuses or bulges that surround the aortic valve, which are called the sinuses of Valsalva. The diameter and orifice area of the aortic root are greater at the vicinity of the sinuses as compared to other portions of the root. With such a complex geometry, implantable grafts matching such complexity have often been made by suturing differently shaped graft components together. For example, U.S. Patent No. 6,352,554 to DePaulis describes a method for forming a graft for the aortic root by suturing a bulbous woven section in between two straight tubular woven sections. Further, the bulbous woven section is also formed cutting or otherwise attaching woven materials. Such techniques are not only costly as numerous textile portions must be sutured to one and the other, but also serve as a potential source for leakage as it is difficult to suture fluid-tight seams among the textile components.

The present invention provides for a seamlessly woven complex grafts including seamlessly woven projections or petals, such as but not limited to aortic root grafts, and methods for producing the same.

SUMMARY OF THE INVENTION

In one aspect of the present invention, an implantable, flat-woven multi-petaled graft is provided. The graft includes (i) a hollow tubular woven portion having opposed first and second tubular ends, the woven portion having a number of warp yarns interlaced with a number of fill yarns in a flat-woven tubular woven pattern to define a flat-woven tubular diameter, and (ii) a bulbous woven portion having opposed first and second ends, the first bulbous end having a greater number of warp yarns interlaced with the fill yarns in a flat-woven tubular bulbous pattern contiguously woven from the second tubular end to provide a seamless woven, wherein the greater number of warp yarns are threadingly engaged with the fill yarns to define a flat-woven bulbous diameter; wherein the second end of the bulbous portion is scalloped with a plurality of petal-like projections seamlessly woven from the first bulbous end. Desirably, the graft of the present invention may include three petal-like projections. The bulbous woven section may be truncated, i.e., hemispherically or hemibulbously shaped The graft of the present invention may be crimped. For example, the tubular portion may be circumferentially crimped. Further, the petal-like projections may be circumferentially crimped.

The graft of the present invention may be ravel resistant, especially the petal-like projections may have edges that are desirably ravel-resistant. The ravel resistant edges may be formed by fusingly sealing the edges. The edges may include heat-fusible yarns. Further, the edges may include an increased yarn density as compared to non-edge portions of the projections. The edges may be woven selvages, or may be cut from the bulbous second end. One method of cutting includes ultrasonic cutting which can also seal the edges from raveling, such as by ultrasonically fusing yarns disposed at the edges.

Desirably, the petal-like projections are contoured. The petal-like projections may be contoured, in part, by threadingly engaging the additional number of warp yarns from the fill yarns. Further, the second end of the bulbous portion may be contoured, in part, by threadingly disengaging the additional number of warp yarns from the fill yarns. The petal-like projections or the bulbous portion may be contoured to mimic the shape of the sinuses of Valsalva.

The tubular woven pattern and the bulbous woven pattern may be selected from, but not limited to, a plain weave, a basket weave, a twill weave, a velour weave, a double velour weave, a satin weave, a terry weave, and combinations thereof. The warp yarns and the fill yarns may include materials, such as polyester, polypropylene, polyethylene, polyurethane, polytetrafluoroethylene and combinations thereof.

Desirably, the warp or fill yarns are single ply, 70 denier, 54 filament, twisted flat polyester; double ply, 40 denier, 27 filament, twisted set polyester; or combinations thereof.

The graft of the present invention may further include a mechanical or tissue heart valve wherein the woven petal-like projections are securably attached to the valve.

In another aspect of the present invention, an implantable prosthesis includes (i) a hollow tubular woven portion having opposed first and second tubular ends, the woven portion having a number of warp yarns interlaced with a number of fill yarns in a flat-woven tubular woven pattern to define a flat-woven tubular diameter; and (ii) a non-tubular woven projection seamlessly transitioned from the second tubular end. The graft may further include a plurality of non-tubular projections seamlessly transitioned from the second tubular end. Desirably, the non-tubular projections are petal shaped.

A method for weaving the graft according to the present invention includes the steps of: (i) weaving a first flat-woven tubular section having opposed open ends and having a number of warp yarns and a number of fill yarns interlaced in a woven pattern to define a first flat-woven diameter; (ii) providing additional warp yarns; (iii) weaving the additional warp yarns into a woven pattern with the number of fill yarns at one of the open ends of the first tubular section to define a bulbous woven section having a second flat-woven diameter, the second diameter being greater than the first diameter; and (iv) scalloping the bulbous woven section to provide a multi-petaled woven end.

The step of scalloping the bulbous end further may further include the step of cutting the bulbous woven portion along longitudinal portions to define edges of a plurality of petal-like projections. The cutting may be ultrasonic cutting. Alternatively, the step of scalloping the bulbous end may further include the step of seamlessly weaving a plurality of petal-like projections extending from the bulbous end. Such weaving may include weaving selvages to define woven edges of the petal-like projections.

The method according to the present invention may further include the step of radially crimping the woven tubular and the woven bulbous sections. Further, the crimping may further include radially crimping the petal-like projections.

The method according to the present invention may further include the steps of (i) providing a mechanical or tissue heart valve; and (ii) attaching the woven petal-like projections to the valve.

BRIEF DESCRIPTION OF THE DRAWINGS

FIG. 1 is a perspective view of a tri-petaled graft of the present invention.

FIG. 2 is a cross-sectional view of the graft of FIG. 1 taken along the 2-2 axis.

FIG. 3 is a cross-sectional view of the graft of FIG. 1 taken along the 3-3 axis.

DETAILED DESCRIPTION OF THE PREFERRED EMBODIMENT

It has been discovered through the present invention that tubular woven textile products such as multi-lobed or multi-petaled vascular grafts can be seamlessly woven into a variety of complex, varied-diameter shapes and sizes, without the need for any post-weaving fabrication techniques such as cutting, sewing, suturing and the like. One method for seamlessly weaving shaped tubular grafts is disclosed in U.S. Pat. No. 5,800,514 to Nunez et al., the contents of which are incorporated herein by reference. This patent describes shaped woven tubular grafts having a gradual woven transition between different sized or shaped tubular graft portions. For the more complex shaped grafts of the present invention such a gradual woven transition, however, may not result in a seamless graft which anatomically matches complex lumen contours, such as the aortic root. One method for weaving such more complexly shaped graft is described in U.S. Parent application Ser. No. 10/823,456 titled "Varied Diameter Vascular Graft" and filed on Apr. 12, 2004, the contents of which is incorporated herein by reference.

FIG. 1 depicts a tri-petaled vascular graft 10 of the present invention. Graft 10 is suitable for replacement of the aortic root, but the present invention is not so limited. Graft 10 includes a first woven tubular section 12 and a varied diameter bulbous woven section 16. Although tubular section 12 is depicted as a straight tubular section, the present invention is not so limited. For example, woven section 12 may also have a varied diameter, for example a tapered shape. Additionally, the bulbous section 16 includes three petals 20a, 20b, 20c. In weaving graft 10 warp yarns extend along the longitudinal direction of graft 10, which is depicted by vector "L". Fill yarns extend circumferentially or radially as depicted by vector "C". Graft 10 is woven as a single structure, i.e., a flat-woven, seamless, varied-diameter, tri-petaled graft. For example, portion 18 of graft 10 is a seamless transition between the woven sections 12 and 16.

As depicted in FIG. 2, the distal end 14 of woven portion 14 is an open end, more particularly a hollow tubular open end. As depicted in FIG. 3 the distal portions of petals 20a, 20b, and 20c are not connected. Further, the diameter $D_1$ of tubular section 12 is desirably less than the diameter $D_2$ of bulbous section 16.

The bulbous section 16 is depicted as a generally spherical section in FIG. 1. The present invention, however, is not so limited, and the bulbous section may have other outwardly extending or flared configurations. For example, the bulbous shape may be oblong. Desirably, the bulbous section 16 or the petal-like projections 20a, 20b, 20c are contoured to mimic the shape of the sinuses of Valsalva.

The graft 10 includes, but is not limited to, a flat-woven tubular portion 12 and a contiguous bulbous woven section 16. The first bulbous end proximal to portion 18 is contiguous with the first tubular portion 12. The tubular portion 12 includes a first number of warp yarns interlaced with a plurality of fill yarns in a woven pattern to define a flat-woven tubular diameter. The bulbous portion 16 has a second number of warp yarns interlaced with the plurality of fill yarns in a woven pattern to define a flat-woven bulbous diameter; wherein the second number of warp yarns is greater than the first number of warp yarns.

Desirably, the bulbous diameter, $D_2$, is from about 2 mm to about 20 mm greater that the first diameter, $D_1$, more desirably, from about 4 mm to about 12 mm, preferably about 8 mm. The first diameter, $D_1$, may vary from about 10 mm to about 50 mm. Useful first diameters include, but are not limited to, 24 mm, 26, mm, 28 mm, 30 mm and 32 mm. Preferred corresponding maximum diameters of the bulbous or sinus region 16 include 32 mm, 34 mm, 36 mm, 38 mm and 40 mm. Desirably, the length of the bulbous section is at least equal to or greater than the diameter, $D_1$, of the straight tubular portion 12.

The woven patterns of the tubular and the bulbous sections, which may be the same or different, include, but are not limited to, a plain weave, a basket weave, a twill weave, a velour weave, a double velour weave, satin weave, terry weave and combinations thereof. Further, yarn density, yarn denier, and yarn type may be constant or may be different between the two woven sections. Useful yarn types include, but are not limited to of multifilament, monofilament, and staple. Useful yarn material, which may be the same or different between the two woven sections, includes, but is not limited to, polyester, polypropylene, polyethylene, polyurethane, polytetrafluoroethylene and combinations thereof.

Desirably, the warp yarns and the fill yarns are polymeric yarns, such as, but not limited to, of polyester, polypropylene, polyethylene, polyurethane, polytetrafluoroethylene and combinations thereof. Preferred warp and fill yarns include single ply, 70 denier, 54 filament, twisted flat polyester; double ply, 40 denier, 27 filament, twisted set polyester; or combinations thereof.

Further, the first bulbous end may include a textile portion having an increasing number of warp yarns at the rate of at least three or more warp yarns for every two of the fill yarns for tubular woven portions and three or more warp yarns for every four of the fill yarns for flat woven fabric portions, such as the petal-like projections, and, optionally, a textile portion having a decreasing number of warp yarns at the rate of at least three warp yarns or greater for every two of the fill yarns for tubular sections or for every four of the fill yarns for the fabric or sheet-like sections. The bulbous section may be formed by threadingly engaging additional warp yarns.

The implantable graft of the present invention may be crimped, either totally or partially. For example, the tubular woven portion may be radially crimped. The bulbous woven portion may be radially crimped. The tubular and the bulbous woven portions may be radially crimped.

The implantable graft of the present invention may further include a mechanical or tissue heart valve securable attached to the second tubular end.

In one aspect of the present invention, an implantable, flat-woven multi-petaled graft is provided. The graft includes (i) a hollow tubular woven portion having opposed first and second tubular ends, the woven portion having a number of warp yarns interlaced with a number of fill yarns in a flat-woven tubular woven pattern to define a flat-woven tubular diameter, and (ii) a bulbous woven portion having opposed first and second ends, the first bulbous end having a greater number of warp yarns interlaced with the fill yarns in a flat-woven tubular bulbous pattern contiguously woven from the second tubular end to provide a seamless woven, wherein the greater number of warp yarns are threadingly engaged with the fill yarns to define a flat-woven bulbous diameter; wherein the second end of the bulbous portion is scalloped with a plurality of petal-like projections seamlessly woven from the first bulbous end. Desirably, the graft of the present invention may include three petal-like projections. The bulbous woven section may be truncated, i.e., hemispherically or hemibulbously shaped The graft of the present invention may be crimped. For example, the tubular portion may be circumferentially crimped. Further, the petal-like projections may be circumferentially crimped.

The graft of the present invention may be ravel resistant, especially the petal-like projections have edges that are desirably ravel-resistant. The ravel resistant edges may formed by fusingly sealing the edges. The edges may include heat-fusible yarns. Such heat-fusible yarns typically include a fiber or part of a fiber, such as a sheath, having a low melting point resin, such as polyethylene. Further details of such yarns and prostheses having such yarns are described in U.S. Pat. No. 5,178,630 to Schmitt, the contents of which is incorporated herein by reference. Further, the edges may include an increased yarn density as compared to non-edge portions of the projections. The edges may be woven selvages, or may be cut from the bulbous second end. One method of cutting includes ultrasonic cutting which can also seal the edges from raveling, such as by ultrasonically fusing yarns disposed at the edges.

Desirably, the petal-like projections are contoured. The petal-like projections may be contoured, in part, by threadingly engaging or disengaging the additional number of warp yarns from the fill yarns. Desirably, the warp yarns change at a rate of at least three or more warp yarns for every four of the fill yarns, which is different from the previously described rate of change for flat woven tubular sections because the petal-like projections are flat-woven fabric or sheets, i.e., not tubular. Further, the second end of the bulbous portion may be contoured, in part, by threadingly disengaging the additional number of warp yarns from the fill yarns. The petal-like projections or the bulbous portion may be contoured to mimic the shape of the sinuses of Valsalva.

The tubular woven pattern and the bulbous woven pattern may be selected from, but not limited to, a plain weave, a basket weave, a twill weave, a velour weave, a double velour weave, a satin weave, a terry weave, and combinations thereof. The warp yarns and the fill yarns may include materials, such as polyester, polypropylene, polyethylene, polyurethane, polytetrafluoroethylene and combinations thereof.

Desirably, the warp or fill yarns are single ply, 70 denier, 54 filament, twisted flat polyester; double ply, 40 denier, 27 filament, twisted set polyester; or combinations thereof.

The graft of the present invention may further include a mechanical or tissue heart valve, wherein the woven petal-like projections are securably attached to the valve.

In another aspect of the present invention, an implantable prosthesis includes (i) a hollow tubular woven portion having opposed first and second tubular ends, the woven portion having a number of warp yarns interlaced with a number of fill yarns in a flat-woven tubular woven pattern to define a flat-woven tubular diameter; and (ii) a non-tubular woven projection seamlessly transitioned from the second tubular end. The graft may further include a plurality of non-tubular projections seamlessly transitioned from the second tubular end. Desirably, the non-tubular projections are petal shaped.

A method for weaving the graft according to the present invention includes the steps of: (i) weaving a first flat-woven tubular section having opposed open ends and having a number of warp yarns and a number of fill yarns interlaced in a woven pattern to define a first flat-woven diameter; (ii) providing additional warp yarns; (iii) weaving the additional warp yarns into a woven pattern with the number of fill yarns at one of the open ends of the first tubular section to define a bulbous woven section having a second flat-woven diameter, the second diameter being greater than the first diameter; and (iv) scalloping the bulbous woven section to provide a multi-petaled woven end.

The step of step of scalloping the bulbous end further may further include the step of cutting the bulbous woven portion along longitudinal portions to define edges of a plurality of petal-like projections. The cutting may be ultrasonic cutting. Alternatively, the step of scalloping the bulbous end may further include the step of seamlessly weaving a plurality of petal-like projections extending from the bulbous end. Such weaving may include weaving selvages to define woven edges of the petal-like projections.

The method according to the present invention may further include the step of radially crimping the woven tubular and the woven bulbous sections. Further, the crimping may further include radially crimping the petal-like projections. Alternatively, the graft of the present invention may be made self supporting with crimping by including a yarn with stiff compound, typically a monofilament yarn, such as a monofilament polyester yarn. Additionally, details are described in U.S. Pat. No. 5,178,630, the contents of which are incorporated herein by reference.

The method according to the present invention may further include the steps of (i) providing a mechanical or tissue heart valve; and (ii) attaching the woven petal-like projections to the valve.

Any type of textile product can be used as the warp yarns and fill yarns of the present invention. Of particular usefulness in forming the woven prostheses of the present invention are synthetic materials such as thermoplastic polymers. Thermoplastic yarns suitable for use in the present invention include, but are not limited to, polyesters, polypropylenes, polyethylenes, polyurethanes and polytetrafluoroethylenes. The yarns may be of the monofilament, multifilament, or stable type.

The yarns used in forming the woven grafts of the present invention may be flat, twisted, textured or set, and may have high, low or moderate shrinkage properties. Additionally, the yarn type and yarn denier can be selected to meet specific properties desired for the prosthesis, such as porosity, flexibility and compliance. The yarn denier represents the linear density of the yarn (number of grams mass divided by 9,000 meters of length). Thus, a yarn with a small denier would correspond to a very fine yarn whereas a yarn with a larger denier, e.g., 1000, would correspond to a heavy yarn. The yarns used with the present invention may have a denier from about 20 to about 1000, preferably from about 40 to about 300. Preferably, the warp and fill yarns are polyester, and most preferably the warp and fill yarns are single ply, 70 denier, 54 filament, twisted flat polyester; double ply, 40 denier, 27 filament, twisted set polyester; or combinations thereof.

The graft of the present invention can be woven using any known weave pattern in the art, including, simple weaves, basket weaves, twill weaves, velour weaves and the like, and is preferably woven using a double velour tubular weave pattern. Details of double velour patterns are described in U.S. Pat. No. 4,517,687 to Liebig et al., the contents of which are incorporated by reference herein. Desirably, the double velour pattern includes a satin weave where a warp yarn crosses over or under at least four fill yarns. The weave patterns may have from about 50-200 warp yarns (ends) per inch per layer and about 30-100 fill yarns (picks) per inch per layer. The wall thickness of the graft may be any conventional useful thickness, for example from about 0.1 mm to about 1.20 mm, desirably from about 0.5 mm to about 0.9 mm.

Such a heat setting process is accomplished by first flat-weaving the graft in a tubular form out of a material capable of shrinking during a heat setting process. After the graft is woven, the graft is placed on a mandrel, and heated in an oven at a temperature and time capable of causing the yarns of the graft to heat set to the shape and diameter of the mandrel. Preferably polyester yarns are used as the warp and fill yarns, and the heat setting is accomplished at time and temperatures appropriate for the material. For example, heat setting can be accomplished at about 190-200° C. for a period of about 14-16 minutes. Other methods of heat setting may be employed, for example ultrasonic heat-setting, or through the use of steam as a heating source. One useful method of ultrasonic heat setting is described in U.S. patent application Ser. No. 10/822,955 titled "Ultrasonic Crimping Of A Varied Diameter Graft" and filed on Apr. 12, 2004, the contents of which are incorporated herein by reference. After heat setting the graft can be formed into a shape desired for implantation.

The invention being thus described, it will now be evident to those skilled in the art that the same may be varied in many ways. Such variations are not to be regarded as a departure from the spirit and scope of the invention and all such modifications are intended to be included within the scope of the following claims.

What is claimed is:

1. An implantable, flat-woven multi-petaled graft comprising:
    a hollow tubular woven portion having opposed first and second tubular ends, said woven portion having a number of warp yarns interlaced with a number of fill yarns in a flat-woven tubular woven pattern to define a seamless tubular woven portion having a flat-woven tubular diameter, and
    a bulbous woven portion having opposed first and second ends, the first bulbous end having a greater number of warp yarns interlaced with said fill yarns in a flat-woven tubular bulbous pattern contiguously woven from said second tubular end to provide a seamless bulbous woven portion, wherein the greater number of warp yarns are threadingly engaged with said fill yarns to define a flat-woven bulbous diameter;
    wherein said second end of said bulbous portion is scalloped with a plurality of petal-like projections seamlessly woven from said first bulbous end;
    wherein the petal-like projections are non-tubular, contoured, lobate-shaped woven sheets having non-connected distal portions.

2. The graft of claim 1, wherein there are three petal-like projections.

3. The graft of claim 1, wherein said tubular portion is circumferentially crimped.

4. The graft of claim 1, wherein said petal-like projections are circumferentially crimped.

5. The graft of claim 1, wherein said petal-like projections are contoured by threadingly disengaging said additional number of warp yarns from said fill yarns.

6. The graft of claim 1, wherein said second end of said bulbous portion is contoured by threadingly disengaging said additional number of warp yarns from said fill yarns.

7. The graft of claim 1, further including a mechanical or tissue heart valve, wherein said woven petal-like projections are securably attached to said valve.

8. The graft of claim 1 wherein said petal-like projections are contoured to mimic the shape of the sinuses of Valsalva.

9. The implantable graft of claim 1, wherein said tubular woven pattern and said bulbous woven pattern are selected from the group consisting a plain weave, a basket weave, a twill weave, a velour weave, a double velour weave, a satin weave, a terry weave, and combinations thereof.

10. The implantable graft of claim 1, wherein said warp yarns and said fill yarns include materials selected from the consisting of polyester, polypropylene, polyethylene, polyurethane, polytetrafluoroethylene and combinations thereof.

11. The implantable graft of claim 1, wherein said warp yarns are single ply, 70 denier, 54 filament, twisted flat polyester; double ply, 40 denier, 27 filament, twisted set polyester; or combinations thereof.

12. The implantable graft of claim 1, wherein said fill yarns are single ply 70 denier, 54 filament, twisted flat polyester; double ply, 40 denier, 27 filament, twisted set polyester; or combinations thereof.

13. The implantable graft of claim 1, wherein said bulbous woven section is hemispherically shaped.

14. The graft of claim 1, wherein said petal-like projections are contoured by threadingly engaging said additional number of warp yarns with said fill yarns.

15. The graft of claim 1, wherein said petal-like projections have edges that are ravel-resistant.

16. The graft of claim 15, wherein said edges are woven selvages.

17. The graft of claim 15, wherein said ravel resistant edges are formed by fusingly sealing said edges.

18. The graft of claim 17, wherein said edges include heat-fusible yarns.

19. The graft of claim 17, wherein said edges include an increased yarn density as compared to non-edge portions of said projections.

20. The graft of claim 15, where said edges are cut from said bulbous second end.

21. The graft of claim 20, wherein said edges are ultrasonically cut from said bulbous second end.

22. The graft of claim 21, where in said edges are ultrasonically sealed by fusing yarns disposed at said edges.

* * * * *